United States Patent [19]

Baudy et al.

[11] Patent Number: 5,541,179
[45] Date of Patent: Jul. 30, 1996

[54] TROPON-2-ONE PIPERAZINE CARBOXAMIDES AS SEROTONERGIC AGENTS

[75] Inventors: Reinhardt B. Baudy, Yardley, Pa.;
Scott C. Berta, New Brunswick, N.J.;
Gary P. Stack, Ambler, Pa.

[73] Assignee: American Home Products Corporation, Madison, N.J.

[21] Appl. No.: 433,639

[22] Filed: May 2, 1995

[51] Int. Cl.[6] ............... A61K 31/55; A61K 31/495; C07D 401/12; C07D 403/12

[52] U.S. Cl. ............... 514/212; 514/252; 540/598; 544/360; 544/364

[58] Field of Search ............... 540/598; 544/360, 544/364; 514/212, 252

[56] References Cited

U.S. PATENT DOCUMENTS

| | | | |
|---|---|---|---|
| 4,988,814 | 1/1991 | Abou-Gharbia | 544/295 |
| 5,271,812 | 12/1993 | Gao et al. | 204/59 R |

FOREIGN PATENT DOCUMENTS

| | | |
|---|---|---|
| 0512755 | 11/1992 | European Pat. Off. . |
| WO9311122 | 6/1993 | WIPO . |
| WO9314076 | 7/1993 | WIPO . |
| WO9421611 | 9/1993 | WIPO . |
| WO9502592 | 1/1995 | WIPO . |

OTHER PUBLICATIONS

J. Bagli, T. Bogri, and K. Voith, J. Med. Chem. 1984, 27, 875–881.

*Primary Examiner*—Emily Bernhardt
*Attorney, Agent, or Firm*—R. F. Boswell, Jr.

[57] ABSTRACT

This invention relates to compounds useful as anxiolytic agents having the formula:

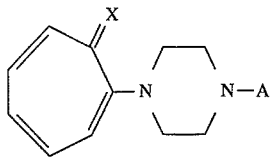

where A is

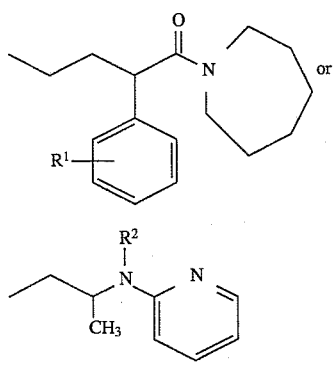

wherein

X is O or S;

$R^1$ is selected from H, —CN, —$OR^3$, —$NO_2$, —$NR^3R^4$, —$NR^3COR^4$, —$NR^3COOR^4$, —$COR^3$, —$COOR^3$, —$CONR^3R^4$, —$SR^3$, —$SOR^3$, —$SO_2R^3$, —$SO_2NR^3R^4$, $C_1$–$C_6$ alkyl, $C_2$–$C_6$ alkenyl, $C_2$–$C_6$ alkynyl, -perhalo-$C_1$–$C_6$-alkyl, F, Cl, Br, and I;

$R^2$ is selected from H, —$COR^3$, —$COOR^3$, —$CONR^3R^4$, —$CONHR^3$, —$COCHR^3R^4$, $C_1$–$C_6$-alkyl, $C_2$–$C_6$ alkenyl, and $C_2$–$C_6$-alkynyl;

$R^3$ and $R^4$ are independently selected from $C_1$–$C_6$-alkyl, $C_2$–$C_6$-alkenyl, $C_2$–$C_6$ alkynyl, benzyl, or phenyl which may be optionally substituted by one to three groups selected from F, Cl, Br, I, —$NO_2$, —CN, and —$C_1$–$C_6$ alkoxy; or $R^3$ and $R^4$ together with the intervening nitrogen form a saturated or unsaturated ring having 4 to 6 carbons and one nitrogen; and or a pharmaceutically acceptable salt thereof.

9 Claims, No Drawings

TROPON-2-ONE PIPERAZINE CARBOXAMIDES AS SEROTONERGIC AGENTS

This invention relates to 4-substituted 1-(tropon-2-yl or thiotropon-2-yl)piperazines which have serotonergic antagonist at the serotonin receptor classified as subtype 1a (5-HT$_{1a}$) and thus, like the classical 5-HT$_{1a}$ antagonist buspirone, have utility as anti-anxiety (anxiolytic) agents.

BACKGROUND OF THE INVENTION

Serotonin (5-hydroxytryptamine or 5-HT) is a neurotransmitter implicated in the etiology or treatment of many medical problems, including anxiety, depression, schizophrenia, hypertension, stroke, migraine, nausea and cognitive deficits. A particular 5-HT receptor in the central nervous system classified as the 5-HT$_{1a}$ receptor has been widely implicated in anxiety and depression. A class of compounds containing the arylpiperazine group bind with the 5-HT$_{1a}$ receptor and have anxiolytic and antidepressant properties in man (Annual Reports in Medicinal Chemistry 27, 21–22 (1992). Buspirone, shown below, is a clinically effective anxiolytic agent.

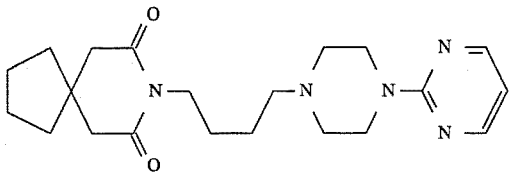

Buspirone

Bagli et al., J. Med. Chem. 27, 875–881 (1984) discloses 1-(2-troponyl)piperazine derivatives which have dopaminergic activity.

SUMMARY OF THE INVENTION

The compounds disclosed herein are 1-(2-troponyl)piperazine derivatives which bind with the 5-HT$_{1a}$ receptors and thus have utility as anxiolytic agents. The compounds of this invention are represented by Formula 1

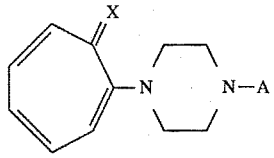

where A is

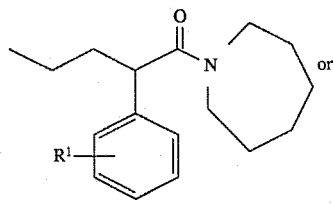

or

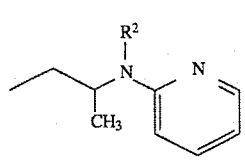

wherein

X is O or S;

R$^1$ is selected from H, —CN, —OR$^3$, —NO$_2$, —NR$^3$R$^4$, —NR$^3$COR$^4$, —NR$^3$COOR$^4$, —COR$^3$, —COOR$^3$, —CONR$^3$R$^4$, —SR$^3$, —SOR$^3$, —SO$_2$R$^3$, —SO$_2$NR$^3$R$^4$, C$_1$–C$_6$ alkyl, C$_2$–C$_6$ alkenyl, C$_2$–C$_6$ alkynyl, -perhalo-C$_1$–C$_6$-alkyl, F, Cl, Br, and I;

R$^2$ is selected from H, —COR$^3$, —COOR$^3$, —CONR$^3$R$^4$, —CONHR$^3$, —COCHR$^3$R$^4$, C$_1$–C$_6$-alkyl, C$_2$–C$_6$ alkenyl, and C$_2$–C$_6$-alkynyl;

R$^3$ and R$^4$ are independently selected from C$_1$–C$_6$-alkyl, C$_2$–C$_6$-alkenyl, C$_2$–C$_6$ alkynyl, benzyl, or phenyl which may be optionally substituted by one to three groups selected from F, Cl, Br, I, —NO2, —CN, and —C$_1$–C$_6$ alkoxy; or R$^3$ and R$^4$ together with the intervening nitrogen from a saturated or unsaturated ring having 4 to 6 carbons and one nitrogen; and or a pharmaceutically acceptable salt thereof.

The pharmaceutically acceptable salts are the acid addition salts which can be formed from a formula 1 compound and a pharmaceutically acceptable inorganic or organic acid such as phosphoric, sulfuric, hydrochloric, hydrobromic, citric, maleic, fumaric, acetic, lactic, or methanesulfonic acid.

The preferred compounds of this invention are those where X is oxygen.

DETAILED DESCRIPTION OF THE INVENTION

The starting tropon-2-ylpiperazine methansulfonate can be prepared according to the procedures of Bagli, et al., J. Med. Chem. 27, 875–881 (1984) as outlined in the following reaction scheme (1) wherein tropolone is methylated with dimethyl sulfate in the presence

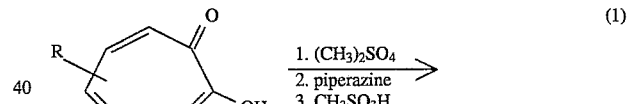

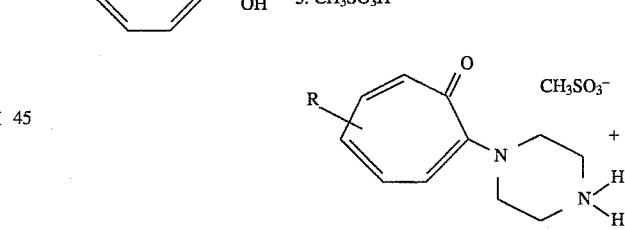

of a suitable base such as potassium carbonate to yield methoxytropon-2-one, which is reacted with piperazine to obtain tropon-2-ylpiperazine which can then be isolated as the crystalline methanesulfonate salt. A formula I compound can be obtained by alkylation of tropon-2-ylpiperazine methanesulfonate with the appropriate alkylating agent in the presence of a base such as diisopropylethylamine as depicted in reaction scheme (2).

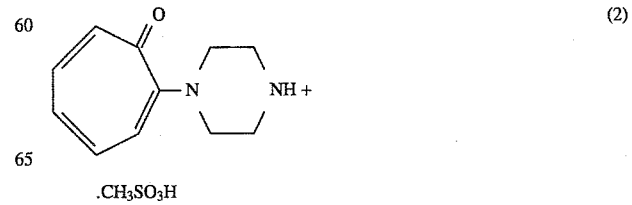

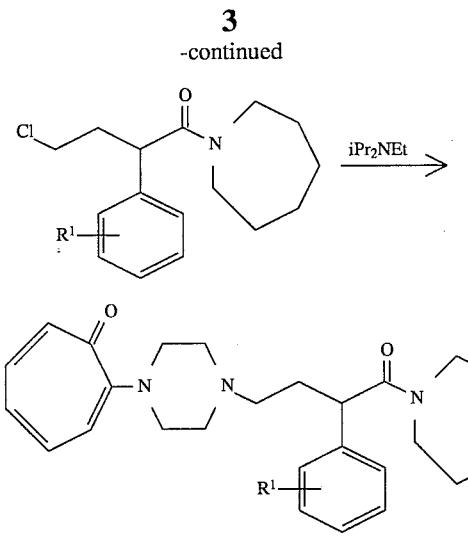

The following specific examples are included to illustrate the synthetic procedures used for preparing the formula 1 compounds. In these examples, all chemicals and intermediates are either commercially available or can be prepared by standard procedures found in the literature and known to those skilled in the art of organic synthesis.

EXAMPLE 1

2-[4-(4-Azepan-1-yl-4-oxo-3-phenyl-butyl)-piperazin-1-yl]-cyclohepta-2,4,6-trienone.

A mixture of piperazin-1-yl-cyclohepta-2,4,6-trienone methanesulfonate salt (0.573 g, 2 mmole), 1-(azepan-1-yl)-4-chloro-2-phenyl-butan-1one (0.616 g, 2.2 mmole), diisopropylethylamine (0.518 g, 4 mmole) and potassium iodide (0.332 g, 2 mmole) in dimethylformamide (20 mL) was heated to 80° C. under dry nitrogen for 4 hours. After cooling the reaction mixture to ambient temperature, water (50 mL) was added and the organic materials extracted with ethylacetate (100 mL). The organic layer was separated, washed with water (2×100 mL) and brine (100 mL), dried over magnesium sulfate, filtered and evaporated in vacuum. The product was isolated by column chromatography on 40 g of silica gel with 2% methanol/chloroform as eluant. Crystallization from ethanol/ether with addition of one equivalent fumaric acid gave 0.3 g of the fumarate salt, m.p. 145°–7° C.

Elemental Analysis for: $C_{27}H_{35}N_3O_2 \cdot C_4H_4O_4$. Calcd: C, 67.74; H, 7.15; N, 7.64. Found: C, 67.55; H, 7.20; N, 7.46.

EXAMPLE 2

(R)-2-{4-[2-(Pyridin-2-ylamino)-propyyl]-piperazin-1-yl}-cyclohepta-2,4,6trienone.

Piperazin-1-yl-cyclohepta-2,4,6-trienone methanesulfonate salt (2.433 g, 8.5 mmole) and (R)-4-methyl-3-(pyridin-2-yl)-[1,2,3]-oxathiazolidine-2,2-dioxide (1.714 g, 8 mmole) were dissolved in dimethylformamide (50 mL) at ambient temperature. Diisopropylethylamine (1.1 g, 8.5 mmole) was added at once and the reaction mixture stirred for 40 minutes at ambient temperature, after which additional diisopropylethylamine (1.1 g, 8.5 mmole) was added and stirring continued for 40 minutes. Dimethylformamide was removed in vacuo and the residue was dissolved in ethylacetate (50 mL) containing water (10 mL). Sulfuric acid conc. (2 g) was added and the reaction mixture stirred for 1 hour at ambient temperature, followed by the addition of sodium hydrogen carbonate (4 g). Stirring was continued at room temperature overnight. The pH of the mixture was adjusted to 10 by adding 0.5 N NaOH and the organic materials extracted with ethylacetate (3×100 mL). The separated organic layer was washed with brine (100 mL), dried over magnesium sulfate, filtered, and evaporated in vacuo. The compound was isolated as the dihydrochloride sesquihydrate salt by crystallization from ether with addition of 1 N ethereal HCl to give 1.5 g, m.p. 128°–32° C.

Elemental Analysis for: $C_{19}H_{24}N_4O \cdot 2$ HCl·1.5 $H_2O$ Calcd: C, 53.77; H, 6.88; N, 13.20. Found: C, 53.74; H, 7.04; N, 12.64.

EXAMPLE 3

Cyclohex-3-enecarboxylic acid (R)-{1-methyl-2-[4-(7-oxo-cyclohepta-1,3,5-trienyl)-piperazin-1-yl]-ethyl}-(pyridin-2-yl)-amide.

A solution of (R)-2-{4-[2-(Pyridin-2-ylamino)-propyl]-piperazin-1-yl}-cyclohepta-2,4,6 trienone (0.59 g, 1.9 mmole) in dry methylene chloride (50 mL) was cooled to 0° C. under exclusion of moisture. A solution of 3-cyclohexenecarbonyl chloride (0.275 g, 1.9 mmole) in dry methylene chloride (10 mL) was added dropwise at 0° C. The reaction mixture was stirred at ambient temperature overnight, then washed with 2.5 N NaOH. The separated organic layer was dried over magnesium sulfate, filtered and evaporated. The compound was purified and isolated as the tri-hydrochloride 1.25 hydrate by column chromatography on 80 g of silica gel with 5% methanol/ethylacetate as eluant, followed by crystallization from ethanol with addition of ethanolic HCl and ether gave 0.6 g of the salt, m.p. 65°–7° C.

Elemental Analysis for: $C_{26}H_{32}N_4O_2 \cdot 3$ HCl·1.25 $H_2O$ Calcd: C, 55.32; H, 6.70; N, 9.93. Found: C, 55.18; H, 6.76; N, 9.73.

EXAMPLE 4

Cyclohexanecarboxylic acid (R)-{1-methyl-2-[4-(7-oxo-cyclohepta-1,3,5-trienyl)-piperazin-1-yl]-ethyl}-(pyrilin-2-yl)-amide.

A solution of (R)-2-{4-[2-(Pyridin-2-ylamino)-propyl]-piperazin-1-yl}-cyclohepta-2,4,6 -trienone (0.59 g, 1.9 mmole) in dry methylene chloride (50 mL) was cooled to 0° C. under exclusion of moisture. A solution of cyclohexanecarbonyl chloride (0.279 g, 1.9 mmole) in dry methylene chloride (10 mL) was added dropwise at 0° C. The reaction mixture was stirred at ambient temperature overnight, then washed with 2.5 N NaOH. The separated organic layer was dried over magnesium sulfate, filtered and evaporated. The compound was isolated as the hydrochloride salt by crystallization from ethanol with addition of ethanolic HCl and ether gave 0.585 g of the title compound, m.p. 62° C.

Elemental Analysis for: $C_{26}H_{34}N_4O_2 \cdot 2$ HCl·2 $H_2O$ Calcd: C, 57.44; H, 7.41; N, 10.30. Found: C, 57.50; H, 7.39; N, 9.78.

EXAMPLE 5

2-[4-(4-Azepan-1-yl-4-oxo-3-(3-methoxyphenyl)-butyl)-piperazin-1-yl]-cyclohepta-2,4,6-trienone.

Following the procedure of Example 1 and substituting an equivalent amount of 1-(azepan1-yl)-4-chloro-2-(3-methoxyphenyl)-butan-1-one for 1-(azepan-1-yl)-4-chloro-2 -phenyl-butan-1-one, the title compound is obtained.

EXAMPLE 6

2-[4-(4-Azepan-1-yl-4-oxo-3-(4-ethoxyphenyl)-butyl)-piperazin-1-yl]-cyclohepta-2,4,6-trienone.

Following the procedure of Example 1 and substituting an equivalent amount of 1-(azepan1-yl)-4-chloro-2-(4-ethoxyphenyl)-butan-1-one for 1-(azepan-1-yl)-4-chloro-2 -phenyl-butan-1-one, the title compound is obtained.

EXAMPLE 7

2-[4-(4-Azepan-1-yl-4-oxo-3-(4-chlorophenyl),butyl)-piperazin-1-yl]-cyclohepta-2,4,6-trienone.

Following the procedure of Example 1 and substituting an equivalent amount of 1-(azepan1-yl)-4-chloro-2-(4-chlorophenyl)-butan-1-one for 1-(azepan-1-yl)-4-chloro-2-phenyl-butan-1-one, the title compound is obtained.

EXAMPLE 8

N-[1-Methyl-2-(4-(7-oxacyclohepta-1,3,5-trienyl)-piperazinyl)ethyl]-N-(2-pyridinyl-benzamide.

Following the procedure of Example 4 and substituting an equivalent amount of benzoyl chloride for cyclohexanecarbonyl chloride, the title compound is obtained.

EXAMPLE 9

N-[1-Methyl-2-(4-(7-oxacyclohepta-1,3,5-trienyl)piperazinyl)ethyl]-N-(2-pyridinyl)-carbamic ethyl ester.

Following the procedure of Example 4 and substituting an equivalent amount of ethyl chloroformate for cyclohexanecarbonyl chloride, the title compound is obtained.

EXAMPLE 10

N-[1-Methyl-2-(4-(7-oxacyclohepta-1,3,5-trienyl)-piperazinyl)ethyl]-N-(2pyridinyl)-N'-phenyl urea.

Following the procedure of Example 4 and substituting an equivalent amount of phenylisocyanate for cyclohexanecarbonyl chloride, the title compound is obtained.

EXAMPLE 11

N-[1-Methyl-2-(4-(7-oxacyclohepta-1,3,5-trienyl)-piperazinyl)ethyl]-N-(2-pyridinyl)-N', N'-dimethyl urea.

Following the procedure of Example 4 and substituting an equivalent amount of dimethylcarbamoyl chloride for cyclohexanecarbonyl chloride, the title compound is obtained.

PHARMACOLOGY

High affinity for the serotonin $5\text{-}HT_{1A}$ receptor was established by testing the claimed compound's ability to displace [$^3$H]8-OHDPAT (dipropylaminotetralin) from the $5\text{-}HT_{1A}$ serotonin receptor following the procedure of Hall et al., J. Neurochem. 44, 1685 (1985). This procedure is employed to analogize this property of the claimed compounds with that of buspirone, which is a standard for anxiolytic activity, and, like the compounds of this invention, displays potent affinity for the $5\text{-}HT_{1A}$ serotonin receptor subtype. The anxiolytic activity of buspirone is believed to be, at least partially, due to its $5\text{-}HT_{1A}$ receptor affinity (Vander Maclen et al., Eur. J. Phamacol. 1986, 129 (1–2) 133–130).

The results of the standard experimental test procedure described in the preceding paragraph were as follows:

| Compound | $5\text{-}HT_{1A}$ Binding ($IC_{50}$) |
| --- | --- |
| Example 1 | 18.6 nM |
| Example 2 | 19.8 nM |
| Example 3 | 861 nM |
| Example 4 | 351 nM |
| Buspirone | 10 nM |

Hence, the compounds of this invention demonstrated affinity for the serotonin $5HT_{1A}$ receptor subtype, and are therefore useful in the treatment of multi-CNS disorders amenable to treatment with antidepressant and anxiolytic agents.

PHARMACEUTICAL COMPOSITION

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myri state. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantifies of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The therapeutically effective dosage to be used in the treatment of a specific psychosis must be subjectively determined by the attending physician. The variables involved include the specific psychosis or state of anxiety and the size, age and response pattern of the patient.

What we claim is:

1. A compound according to Formula I

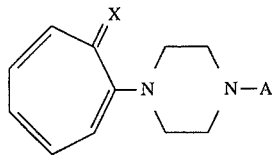

where A is

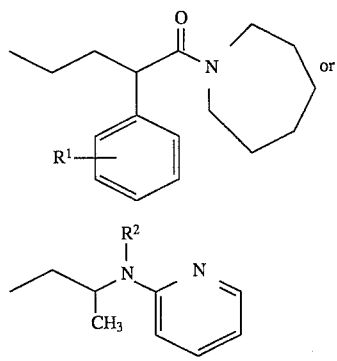

wherein

X is O or S;

$R^1$ is selected from H, —CN, —$OR^3$, —$NO_2$, —$NR^3R^4$, —$NR^3COR^4$, —$NR^3COOR^4$, —$COR^3$, —$COOR^3$, —$CONR^3R^4$, —$SR^3$, —$SOR^3$, —$SO_2R^3$, —$SO_2NR^3R^4$, $C_1$–$C_6$ alkyl, $C_2$–$C_6$ alkenyl, $C_2$–$C_6$ alkynyl, -perhalo-$C_1$–$C_6$-alkyl, F, Cl, Br, and I;

$R^2$ is selected from H, $C_1$–$C_6$-alkyl, $C_2$–$C_6$ alkenyl, and $C_2$–$C_6$-alkynyl;

$R^3$ and $R^4$ are independently selected from $C_1$–$C_6$-alkyl, $C_2$–$C_6$-alkenyl, $C_2$–$C_6$ alkynyl, benzyl, or phenyl which may be optionally substituted by one to three groups selected from F, Cl, Br, I, —$NO_2$, —CN, and —$C_1$–$C_6$ alkoxy; or $R^3$ and $R^4$ together with the intervening nitrogen form a saturated or unsaturated ring having 4 to 6 carbons and one nitrogen; and or a pharmaceuticlly acceptable salt thereof.

2. A compound according to claim 1 wherein X is oxygen.

3. A compound according to claim 2 which is:

2-[4-(4-Azepan-1-yl-4-oxo-3-phenyl-butyl)-piperazin-1-yl]-cyclohepta-2,4,6-trienone.

4. A compound according to claim 2 which is:

(R)-2-{4-[2-(Pyridin-2-ylamino)-propyl]-piperazin-1-yl}-cyclohepta-2,4,6-trienone.

5. A method of treating anxiety in a mammal which comprises administration to a mammal in need thereof a therapeutically effective amount of a compound having the formula:

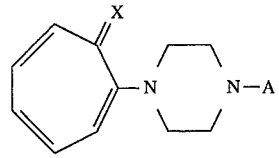

where A is

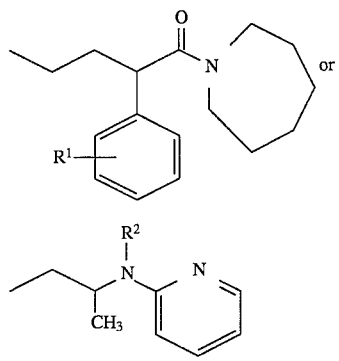

wherein

X is O or S;

$R^1$ is selected from H, —CN, —$OR^3$, —$NO_2$, —$NR^3R^4$, —$NR^3COR^4$, —$NR^3COOR^4$, —$COR^3$, —$COOR^3$, —$CONR^3R^4$, —$SR^3$, —$SOR^3$, —$SO_2R^3$, —$SO_2NR^3R^4$, $C_1$–$C_6$ alkyl, $C_2$–$C_6$ alkenyl, $C_2$–$C_6$ alkynyl, -perhalo-$C_1$–$C_6$-alkyl, F, Cl, Br, and I;

$R^2$ is selected from H, $C_1$–$C_6$-alkyl, $C_2$–$C_6$ alkenyl, and $C_2$–$C_6$-alkynyl;

$R^3$ and $R^4$ are independently selected from $C_1$–$C_6$-alkyl, $C_2$–$C_6$-alkenyl, $C_2$–$C_6$ alkynyl, benzyl, or phenyl which may be optionally substituted by one to three groups selected from F, Cl, Br, I, —$NO_2$, —CN, and —$C_1$–$C_6$ alkoxy; or $R^3$ and $R^4$ together with the intervening nitrogen form a saturated or unsaturated ring having 4 to 6 carbons and one nitrogen; and or a pharmaceuticlly acceptable salt thereof.

6. A method of treatment according to claim 5 where, in the compound used, X is oxygen.

7. A method of treatment according to claim 6 wherein the compound used is:

2-[4-(4-azepan-1-yl-4-oxo-3-phenyl-butyl)-piperazin-1-yl]-cyclohepta-2,4,6-trienone.

8. A method of treatment according to claim 6 wherein the compound used is:

(R)-2-{4-[2-(pyridin-2-ylamino)-propyl]-piperazin-1-yl}-cyclohepta-2,4,6-trienone.

9. A pharmaceutical composition useful for the treatment of anxiety which comprises a pharmaceutically acceptable carrier and a therapeutically effective amount of a compound having the formula:

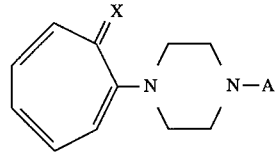

where A is

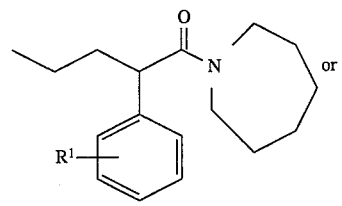

-continued

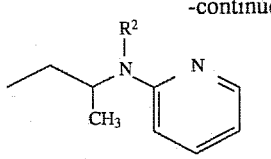

wherein

X is O or S;

R$^1$ is selected from H, —CN, —OR$^3$, —NO$_2$, —NR$^3$R$^4$, —NR$^3$COR$^4$, —NR$^3$COOR$^4$, COR$^3$, —COOR$^3$, —CONR$^3$R$^4$, —SR$^3$, —SOR$^3$, —SO$_2$R$^3$, —SO$_2$NR$^3$R$^4$, C$_1$–C$_6$ alkyl, C$_2$–C$_6$ alkenyl, C$_2$–C$_6$ alkynyl, -perhalo-C$_1$–C$_6$-alkyl, F, Cl, Br, and I;

R$^2$ is selected from H, C$_1$–C$_6$-alkyl, C$_2$–C$_6$ alkenyl, and C$_2$–C$_6$-alkynyl;

R$_3$ and R$^4$ are independently selected from C$_1$–C$_6$-alkyl, C$_2$–C$_6$-alkenyl, C$_2$–C$_6$ alkynyl, benzyl, or phenyl which may be optionally substituted by one to three groups selected from F, Cl, Br, I, —NO$_2$, —CN, and —C$_1$–C$_6$ alkoxy; or R$^3$ and R$^4$ together with the intervening nitrogen form a saturated or unsaturated ring having 4 to 6 carbons and one nitrogen; and or a pharmaceutically acceptable salt thereof.

* * * * *